United States Patent
Abri

(10) Patent No.: US 8,452,615 B2
(45) Date of Patent: May 28, 2013

(54) METHOD AND SYSTEM FOR MANAGEMENT OF OPERATING-ROOM RESOURCES

(75) Inventor: Omid Abri, Berlin (DE)

(73) Assignee: How to Organize (H2O) GmbH (DE)

( * ) Notice: Subject to any disclaimer, the term of this patent is extended or adjusted under 35 U.S.C. 154(b) by 570 days.

(21) Appl. No.: 12/270,507

(22) Filed: Nov. 13, 2008

(65) Prior Publication Data

US 2009/0125337 A1     May 14, 2009

Related U.S. Application Data

(60) Provisional application No. 60/987,590, filed on Nov. 13, 2007.

(30) Foreign Application Priority Data

Nov. 13, 2007 (EP) ..................... 07022003
Nov. 11, 2008 (EP) ..................... 08019690

(51) Int. Cl.
*G06Q 10/10*     (2006.01)
*G06Q 50/22*     (2006.01)

(52) U.S. Cl.
CPC .................... *G06Q 50/22* (2013.01)
USPC ................................... 705/3; 705/2

(58) Field of Classification Search
USPC ........................................... 705/3
See application file for complete search history.

(56) References Cited

U.S. PATENT DOCUMENTS

| | | | |
|---|---|---|---|
| 4,937,743 A * | 6/1990 | Rassman et al. | ................. 705/8 |
| 5,732,401 A | 3/1998 | Conway | |
| 5,996,889 A | 12/1999 | Fuchs et al. | |
| 6,223,137 B1 | 4/2001 | McCay et al. | |
| 6,581,117 B1 | 6/2003 | Klein et al. | |
| 2002/0055918 A1 * | 5/2002 | Hlathein et al. | ................. 707/1 |
| 2002/0116300 A1 * | 8/2002 | DeBusk et al. | ................. 705/29 |
| 2002/0131572 A1 | 9/2002 | Paradis | |
| 2003/0149598 A1 | 8/2003 | Santoso et al. | |
| 2004/0186683 A1 | 9/2004 | Farber et al. | |
| 2005/0166239 A1 | 7/2005 | Uchikubo et al. | |
| 2006/0173713 A1 | 8/2006 | Petro et al. | |

FOREIGN PATENT DOCUMENTS

| | | |
|---|---|---|
| DE | 19904090 A1 | 8/2000 |
| EP | 1068837 | 1/2001 |
| EP | 1769771 A1 | 4/2007 |
| WO | 9725682 | 7/1997 |

(Continued)

OTHER PUBLICATIONS

European Search Report; EP 08 01 9690; Dec. 23, 2008; 4 pages.

(Continued)

*Primary Examiner* — Hiep V Nguyen
(74) *Attorney, Agent, or Firm* — St. Onge Steward Johnston & Reens LLC

(57) ABSTRACT

A computer-implemented method for managing operating-room resources in a hospital includes the steps of receiving at least one surgery request, identifying the resources required for surgery associated with the surgery request, capturing initial data on availability of the resources, capturing initial patient data, and establishing a pre-scheduled operating-room plan based on an initial optimization, and the further steps of capturing current data on availability of the resources, capturing current patient data and establishing a current operating-room plan based on a current optimization. A computer-based system for managing operating-room resources in a hospital and a modular computer-based system for managing operating-room related processes in a hospital are also disclosed.

12 Claims, 4 Drawing Sheets

FOREIGN PATENT DOCUMENTS

| | | |
|---|---|---|
| WO | 9966444 A1 | 12/1999 |
| WO | 0057336 A1 | 9/2000 |
| WO | 03025703 A2 | 3/2003 |
| WO | 2005087125 A2 | 9/2005 |
| WO | 2006081041 A2 | 8/2006 |

OTHER PUBLICATIONS

European Patent Office Examination Report; Application No. EP 07 022 003.3; Jan. 14, 2010; 10 pages.

European Search Report, dated Jun. 13, 2008, 10 pages.

* cited by examiner

METHOD AND SYSTEM FOR MANAGEMENT OF OPERATING-ROOM RESOURCES

CROSS-REFERENCE TO RELATED APPLICATIONS

The present application claims the benefit under 35 U.S.C. §119(e) of the U.S. Provisional Patent Application Ser. No. 60/987,590, filed on Nov. 13, 2007. The present application also claims priority of European patent application Nos. 07 022 003.3 filed on Nov. 13, 2007 and 08 019 690.0 filed on Nov. 11, 2008. All prior applications are herein incorporated by reference in their entirety.

FIELD OF THE INVENTION

The present invention relates to a method and system for management of operating-room (OR) resources in a hospital, to a computer-based system for managing OR resources in a hospital, and to a modular system for management of OR-related processes in a hospital.

BACKGROUND OF THE INVENTION

A method and system for scheduling appointments between a patient's schedule and the schedules of required resources in a hospital are disclosed in US 2002/0131572 A1. The system includes a server including a local memory, a client, and a database, with a patient schedule and a resource schedule being loaded from the database into the local memory for determining available times for the resource schedule. The method and system do not include management of medical devices.

An integrated medical device and healthcare information system is disclosed in US 2006/0173713 A1. The healthcare information system (HIS) includes a scheduling system for scheduling a medical procedure for a particular patient. A workflow management system communicates with a peripheral management system and with a data base, in order to create and schedule the patient workflow. Based on the diagnosis and treatment plan for an individual patient, medical devices are automatically pre-configured. The system does not include multi-resource planning as required for scheduling operating rooms.

According to a method and system for assignment, scheduling and notification as disclosed in US 2003/0149598 A1, patients are automatically assigned to at least one registered clinician, and event tasks are generated for the clinician. If the clinician is unavailable as determined by a scheme of priorities, the event task is assigned to another registered clinician. The clinicians are assigned mobile transceivers coupled to the system via known wireless networking protocols. Event tasks can be initiated by medication and procedure alarms, by patient monitoring devices or voice or position detection, or by lab-result availability. The system does not provide for multi-resource planning for scheduling operating rooms.

A method of optimal scheduling of a plurality of medical procedures by a plurality of surgeons in a set of operating rooms is disclosed in WO 97/25682. The scheduling is done and optimized based on required resources, including preferences and availabilities, and cost functions, taking into account the total cost associated with each feasible schedule. Optimization is activated 48 or 72 hours before the day of surgery, and variations between the optimal schedule and actual conditions in the operating rooms during that day may be accounted for in a revised schedule for the medical procedures during that day.

Known methods and systems provide schedules for tasks, processes, and resources in hospitals. Those schedules are optimized based on initial conditions, and may be adapted due to a particular alarm. However, processes in an operating room are particularly complicated due to the involvement of a multiplicity of personnel, devices, and contributory processes, such as device and patient preparation, medical data presentation etc. Moreover, OR planning is particularly susceptible to emergency situations arising from inside or outside the OR, or to changes enforced by conditions of patients or by other circumstances.

Therefore, it is the object of the present invention to provide a method and system for management of OR resources that includes multi-resource planning and permits an automatic adaptation of schedules to current requirements and situations.

It is a further object of the present invention to provide a modular system for management of processes in or relating to an operating room, in particular in a hospital, that may include multi-resource planning and permit an automatic adaptation of schedules to current requirements and situations.

SUMMARY OF THE INVENTION

The present invention provides, in accordance with claim 1, a method for managing operating-room resources in a hospital, wherein at least one surgery request is received, the resources required for surgery associated with the surgery request are identified, initial data on availability of the resources are captured, initial patient data are captured, and a pre-scheduled operating-room plan is established based on an initial optimization, wherein further current data on availability of the resources are captured, current patient data are captured, and a current operating-room plan is established based on a current optimization. Preferably, the method is performed employing an electronic computing device, in particular a computer.

The method according to claim 1 may be started at any time. Preferably, initial OR resource planning for a given day is accomplished well in advance of that day, e. g., 2 or 3 days in advance. Thus, the method of planning OR resources may be started on a regular basis, e. g. daily, referring to a given day in the future. In this case, there may be one or several surgery requests available for processing at the point of time when the method is started. Alternatively, the method may also be triggered by certain events, e. g. by a manual interaction, or by a surgery request itself.

A surgery request may be any kind of medical demand relating to the use of an operating room (OR). Surgery requests may be initiated manually by, e. g., a physician, or automatically, e. g. by an administrative process in the hospital such as the admission of a patient. Surgery requests may be entered by a user interface into a computer on which the method is implemented, or transferred to the computer by data transfer means such as a computer network. A surgery request may be compulsory as well as tentative, may be associated to a fixed time, to a preferred time, or open to delay within a certain range; surgery requests may also be associated with priority levels, according to the kind of surgery and to the severity of the case. According to the invention, all those data may be captured and employed for subsequent processing.

Each surgery request is associated with a particular kind of surgery, which is associated with certain resource requirements. Such resources (denoted "operating-room resources") may be, e. g.,

- the OR itself, which may be particularly equipped for special kinds of surgery,
- the operating doctors who may be specialized on particular kinds of surgery,
- anaesthetists and qualified nurses,
- trays with the necessary instruments,
- additional instruments,
- medication, implants and disposables,
- therapeutic and diagnostic devices.

Those resources are identified based on the basis of a dedicated data base established in advance in a particular hospital, or on the basis of a publicly available data base or on the basis of general medical standards. However, there can be preferences by individual physicians, concerning, e. g., instrumentation, patient bedding or operating room setups, which may be accounted for in the following planning steps. Data on resources, preferences, etc. may be stored in a computer-readable memory and provided to a computer on which the method is implemented.

Information on doctors' preferences may be gathered from individual profiles for every doctor. If, e. g., a particular surgeon prefers special instruments for a certain operation, those instruments will be identified and, if the doctor is scheduled for a certain operation, the availability of those instruments will be automatically checked during further processing. Some operations require a particular OR setup or a particular bedding type, i. e. a particular way the patient is bedded on an operating room table; this will then be automatically indicated and corresponding resources identified. Other operations allow several alternative bedding types or OR setups; in these cases, the operating doctor's preferences are automatically checked, and the preferred bedding type is indicated and accounted for in planning.

According to the present invention, initial data on the availability of the resources identified are captured for further processing. In particular, in order to schedule doctors and nurses, the calendars of doctors and nurses are accessed and integrated. This integration additionally guarantees that vacations and other absence times are taken into account. After planning has been done, the scheduled times may be entered automatically into those calendars. In that way a two-way synchronization of planned activities and available times of responsible personnel is achieved. Preferably, these calendars can be accessed via workstations in the hospital, via a wireless local area network (WLAN) in the hospital through portable devices, such as laptops and personal digital assistants (PDAs), and/or via an internet connection from outside the hospital.

Moreover, for every mobile therapeutic and diagnostic device a calendar may be established and employed in further processing in order to verify availability.

Data on availability of trays and additional instruments may be accessed from an instrument management module, which will be described below. Thus, it is assured that the required instruments are available at the scheduled date and time.

Data on availability of disposables are preferably accessed through a connection to the material management system of the respective hospital. While planning, stock quantities may be checked and compared to quantities normally used in the specific operation.

According to the present invention, initial patient data are captured for further processing, in particular any kind of patient data relevant for the particular operation. Thus, patient data may include any kind of medical information on the patient, on the particular indication necessitating surgery, personal data, but also additional information on the patient, e.g. allergies, general health condition, etc. Those data can be accessed through interfaces to electronic patient records or to the hospital information system. Patient data may indicate additional or special resource requirements for that particular patient, e. g., particular devices or medication for anaesthesia, particular instruments adapted to size or other physical properties of the patient, bedding requirements, etc. Preferably, the availability of those resources will be determined as well, and those resources will also be included in the subsequent planning and optimization.

In order to establish a pre-scheduled OR plan, an initial optimization is conducted, employing the initial data captured. For scheduling an operation, the constraints connected to the specific operation (e.g. endoscopic gallbladder resection) are scanned and only dates and times are offered on which all constraints are fulfilled or are fulfilled to the highest degree. Constraints to be considered comprise, in particular, the availability of required resources.

If there is more than one department or discipline having access to the operating room or rooms, for every operation room slots are distributed among the operating departments or disciplines in the hospital. The slots represent the assigned times to be planned by different disciplines for operations, including preferred starting times and expected durations of operations. Preferably, the slots are frequently redistributed, depending on the actual and planned utilization of these slots and according to the general utilization of the hospital. Doctors can plan operations in these assigned slots.

Scanning of constraints is done with a solver engine, which is integrated in the system on which the method is implemented. The solver weighs the different requests against each other and uses mathematical optimization to find the best solution for the given problem. The weights assigned to the request may represent medical aspects, such as medical severity or urgency of the surgical operation, but also technical or economic aspects, e. g. giving priority to surgeries which had been scheduled for an earlier date but were deferred, or preferring an early starting time for operations of exceedingly long or unpredictable duration.

This planning step can be done on a long-term basis well in advance of the planned surgery. The optimization strategy applied in this planning phase is static, which means that scheduling is optimized based on the initial availability of resources, without influence of the current state.

In the next planning step, a current OR plan is created in detail close to the planned operations, preferably at the beginning of each day, employing current data. To this end, current data on the availability of resources for each scheduled operation are captured, as well as current patient data, including current health information. The constraints for each scheduled operation are checked on a current basis, and an optimized current plan is developed and offered. If any changes are needed to be made, for example due to changing conditions of a patient, preferably those changes can be entered through a user interface displaying the various surgical operations on a screen and allowing drag and drop movement of operations. The validity of these changes can be verified instantly, and conflicts can be displayed and possible alternatives proposed in order to achieve an optimal schedule. After all rescheduling is done the plan is finished and set on running. After this step the plan can be printed and transferred for further processing, as described below.

Further features and benefits are reliability of scheduling, increased transparency, optimized utilization of operating rooms, reduced operating cost, reduced downtime, and reduced duration of hospital stays. Reports generated in accordance with invention may include the status quo per operating room, as well as, e. g., the planned consultation of patients, and the planned surgeries per discipline.

The method according to the present invention may permit planning of one or more operating rooms. Preferably, the level of detail of planning can be adjusted according to the requirements of the hospital. The lowest level of detail should include at least: patient, operating room and operating doctors. Additional details that may be included are, e. g., required personnel for the operation, including special qualifications of every person contributing to the operation, such as special nurse training for the specific operation. Furthermore, instruments, trays, implants, medication, required anaesthetics, required disposables, required diagnostic and therapeutic devices (e.g. x-ray machines, laparoscopic cameras, etc.) can be included in the planning process.

In a preferred embodiment of the present invention, emergency requests can be received and, according to an emergency management strategy, a revised current OR plan is established that accounts for the emergency requests. In this way, according to an emergency management strategy, flexible planning can be achieved coping with critical changes as they arise.

In the emergency management strategy new patients can be added to the schedule and are planned according to emergency indicators. The patients get an operation slot according to an indicator; this indicator may be influenced by the patient condition, its vital parameters and can also be based on doctor's decisions. According to the indicator the patient is scheduled in an operation slot and other patients with lower indicators are moved.

In a further embodiment of the invention, the OR plan is continually revised on a real-time basis. This includes capturing data on availability of resources, capturing patient data, and conducting optimization, all on a real-time basis. The OR plan is either re-calculated on a short-term basis, say, every few seconds or minutes, or as soon as any new event or change are received. In this way, the OR plan responds to changing situations as fast as possible. In particular, emergency requests can be included. A real-time OR plan assures optimal utilization of resources, in particular optimal utilization of ORs, optimal flexibility, and optimal response to changing requirements and emergency situations.

Preferably, clinical pathways can be defined in a flexible manner according to the needs of the hospital. Clinical pathways are standardized pathways for the treatment of a patient with a certain diagnosis. They provide a description through which treatment steps the patient should go and under which circumstances additional steps are needed. Such pathways can be always updated with newest research results and give an orientation for the personnel.

Clinical pathways, surgeries, and/or other processes in a hospital can be broken down into individual tasks. Such tasks can be pre-defined, relating to particular resources. In the planning process, tasks can be assigned to individuals and can be given starting and finish times. E. g., a patient scheduled for an operation has to be transported to anaesthesia a certain time before the scheduled operation. The task of transporting the patient can be assigned to a nurse, and the time required for transport can be calculated based on patient and other data. Therefore, once the operation is scheduled, starting and finish time for the task of transporting the patient can be calculated.

In a similar way, other processes contributing to operations can be broken down into tasks, and these tasks can be scheduled. Such OR-related processes include, e. g., inducing anaesthesia, providing, preparing and pre-setting of surgical devices, preparation and set-up of the OR, providing surgical instruments, providing and displaying patient or medical information etc. Post-OR processes, such as post-anaesthesia care, post-operative intensive care, cleaning and/or sterilization, waste disposal, reporting, etc, can be scheduled in a similar way. Thus, an OR-related process may be the surgical procedure itself, e. g., an endoscopic gallbladder resection. On the other hand, preparatory and auxiliary procedures are also considered OR-related processes, such as, e. g., selecting and providing surgical, e. g. endoscopic instrumentation for the requested surgery, selecting, providing, configuring, starting and pre-adjusting surgical devices such as light sources, insufflation and electrosurgical devices, etc., patient preparation, transport, and anaesthesia, patient data displaying, etc.

Post-operative processes and resources may also have an influence on the OR plan—thus, e. g., if there is no vacancy in the intensive care unit, those operations which have a high probability of the patient requiring post-operative intensive care may be delayed, possibly subject to emergency indicators. The overall process of surgical operation and one or more preparatory or auxiliary processes is also considered an OR-related process.

In a further embodiment of the invention, the data on availability of resources include real-time data on at least one operating-room related process. Such data represent the actual progress of that process. In particular, data on an operating-room related process may include information on the completion of individual tasks contained in that process. Such information may be required from a person responsible for the task. Lack of delay of completion information may indicate the necessity of a corrective action, or even delay of the process, which may require an adaptation of the OR schedule.

In this way, possible delays can be detected at a very early point of time and, if possible, consequences on the OR schedule can be avoided or immediately considered in an updated OR schedule. Thus, a very short-time reaction is possible, and there is always an automatic optimization of the plan.

Preferably, the data on said operating-room related process include data on deviations of the process from a pre-determined process path. Such a pre-determined process path may include, in addition to starting and finish times of individual tasks into which the process can be split up, locations of resources at the starting or end points of the process or of individual tasks, or even a set of pre-determined locations during the process or the tasks. The set of pre-determined locations may be associated with a corresponding time frame, depending on the actual scheduling. Thus, e. g., the task of transporting a patient to an OR may have a pre-determined path by defining a sequence of rooms and passages. Deviation from that sequence, e. g. by erroneously transporting the patient to another OR than scheduled, may trigger a corrective action.

The deviations from the pre-determined process path may be automatically detected, in particular by means of a location monitoring system. Such a location monitoring system, which may be part of an OR steering and localisation system, locates required staff and equipment resources. In particular, the location motoring system permits locating and/or tracking any staff, patients, mobile devices, beds, and/or further items relevant to hospital processes. This may be accomplished by a single or by a combination of different location technologies. In this way, resource usage can be managed in order to allow flexible planning, and real-time, task-driven control of operating room processes.

Through the integration of task management and tracking every deviation can be automatically detected and the future activities are automatically rescheduled accordingly. Thus, there is an automatic optimization for every deviation from the plan. For this optimization strategy a solver engine is applied. While for the creation of the initial plan a static optimization strategy is applied, the optimization strategy applied in this step is dynamic. For every deviation from the clinical pathway or for a certain task the daily plan is recalculated and optimized. If any conflicts arise, for example that it is impossible to conduct an operation in a given time frame, alternatives are proposed. This approach permits real-time task-driven control, optimal resource management, and identification and elimination of bottlenecks, such as lack of OR availability or unavailable staff.

As there usually is a wireless local area network installed in a hospital, this can be the basis for the tracking technology. Tracking with wireless LAN is typically done with so called site maps. After a WLAN network comprising a number of access points has been installed, a site survey is done, where the information of all access points of the hospital is connected with location information, thus creating a site map. Every device communicating via the WLAN is able to determine its location on the basis of access points from which signals can be received and at which respective strengths. With this technology an accuracy of up to 2 meters can be achieved.

In order to improve accuracy, WLAN tracking may be combined with other location technologies, such as infrared light location, active RFID gates or others.

Preferably, data from other location technology available in the respective hospital are accessed via flexible interfaces. These interfaces provide a configurable setting in order to connect the available technologies to the system without extensive configuration. This can be achieved through an interface which converts the location data from the location technology into a format compatible to the present system.

Preferably, not only dedicated location tags can be tracked, but also devices normally used in a hospital based on the integrated WLAN chip, such as Laptops, PDAs and mobile phones. This can be done with software that is installed on the dedicated device, which monitors the location information received by the device and sends this information to the location interface. The interface calculates the location of the device based on the site map and connects this information with the data from the clinical pathway.

In a further embodiment of the invention, in case of a deviation from the pre-determined pathway, a notification is transmitted to a communication device related to the deviation. Such notifications may be limited to severe deviations of location and/or time exceeding given thresholds. This permits minimization of deviations and therefore keeping to the optimal schedule. The notification may be an alert, an alarm, information on a possible corrective action such as return on the prescribed path, etc. The communication device may be fixed to the device the pathway of which is monitored, may be a communication device of the responsible person, or may be near the location where the deviation has been detected.

Preferably, staff communication and/or nurse call is enabled by the communication device, most preferably via internet protocol (VOIP). This may also permit the transmission and display of patient data. Thus, information is accessible not only via the laptops, tablet PCs and workstations but also through mobile devices, such as mobile phones and PDAs.

In accordance with claim 8, the present invention provides a computer-based system for managing operating-room related processes in a hospital, in particular for managing OR-related resources. The system comprises at least one computer, configured for performing a method as described above. In this way, the system is able to account for the complex requirements associated with the management of operating rooms and to provide optimized OR schedules.

The system may comprise at least one user interface for receiving user commands, concerning, e. g., surgery requests or preferred or compulsory resource or time requirements, and for displaying an OR plan and related schedules, such as schedules for staff, equipment, instruments, materials etc. The system may also comprise one or several interfaces for communicating with one or a multiplicity of further systems. Such communication may serve the acquisition of data provided by such further systems, such as patient data or real-time data on the status of OR-related processes. On the other hand, data generated by the system may be transmitted to other systems, such as updated patient data, equipment and instrument usage data, or data on consumption of disposables. Moreover, the system may comprise storage means or an interface providing access to a data base that includes data on operations, resources, preferences, etc., to be employed in the method described.

In accordance with claim 9, the invention further provides a modular system for managing operating-room related processes in a hospital. The system includes a control unit for operating a process control bus for controlling at least one operating-room related process in a hospital, the control unit being connectable in a modular manner to a multiplicity of modules, and at least one of a multiplicity of modules operatively connected to the control unit, each module controlling at least one task in an operating-room related process in a hospital. Preferably, the modules are self-contained hardware or software units, having well-defined interfaces to other units, which can be combined in various combinations to form an integrated system. Modularity may be achieved, e. g., by means of a self-configuring bus system. The modular system has the advantage of being easily adaptable to the particular needs of every hospital.

Operating-room related processes are those processes in a hospital or other medical facility which comprise usage of an operation room, i. e., which comprise, in particular, a surgical operation, or are otherwise related to the OR, e. g., being a prerequisite or a consequence of a surgical operation. Thus, an operating-room related process is, e. g., a surgical operation itself, the preparation of a patient for surgery, or the post-operative patient care. Other operating-room related processes are the preparation and providing of surgical instruments, implants, disposables, or other equipment, the cleaning and sterilisation of instruments and equipment or the treatment of waste. The combination of two or more of those processes will also be considered an operating-room related process.

The process control bus is designed to organize and direct the functions of the other equipment and modules. It also provides intelligent integration of the various components as well as with hospital information systems. By providing effective coordination of the resources and applications used during surgery, it delivers optimized control of resources to increase efficiency, enhance quality and help reduce cost. It also provides for reports on the resources used for surgical procedures, documenting, analyzing, and evaluating data related to other modular components, e. g. on management, quality, anaesthesia and instrument related data. The report functions may be freely definable by the user, and may analyze generated data in real time, providing valuable feedback to promote optimal efficiency and comprehensive planning. Preferably, the process control bus supports standard interfaces such as, e. g., HL7, to a hospital information system and/or to outside communication partners. In a preferred mode, it operates via a wire-based or wireless computer network.

According to the present invention, the process control bus provides centralized control of one or several hardware and/or software modules and control systems, including, but not limited to the following:
- OR resource planner module
- OR steering and localisation module
- OR instrument management module
- OR document management module
- OR anaesthesia management module According to a preferred embodiment, the modular system includes a computer on which can be run the method for management of OR resources as described. The computer may be the control unit itself or another computing unit or a multiplicity of computing units. In particular, the OR resource planning can be performed by an OR resource planner module configured for planning operating-room resources according to the method described above.

The OR resource planner module facilitates planning of the highly complex OR department. While an operation is planned, the system controls the availability of all necessary resources. Thereby resource conflicts are avoided and scheduling is facilitated. The presence of personnel and of mobile therapeutic and diagnostic devices may be verified by an OR steering and localization module, and the availability of instruments may be verified by an OR instrument management module. Thus, verification is achieved through the holistic approach of the present invention.

Preferably the system allows synchronization of patient, diagnosis and treatment data from the Hospital Information System (HIS). For this synchronization the system preferably uses different interfaces. These interfaces can be based on standards, such as Health Level 7 (HL7). The system may also provide a variety of vendor-specific interfaces. Synchronization of data may be possible in both ways. Thus, the system is able to gather information from electronic patient records and the HIS, but the system will as well provide an update to the HIS patient data and status including information from the operation.

According to a preferred embodiment of the present invention, the system includes a task management system, which creates and manages task lists for every person involved in clinical pathways. Each clinical pathway that includes different steps for diagnosis and treatment is broken down in tasks with a defined time frame. The task management system automatically creates tasks for every patient that needs treatment in the hospital and distributes these among the active personnel. These tasks are then distributed among the personnel currently on duty and shown in their respective task lists. During the creation of these task lists not only the time and resources needed for the certain task are considered, but also e.g. the time that is needed to get from one place where a task is fulfilled to the next place. These transfer times are automatically collected and calculated from the system during operation.

Preferably the task management system is connected to the mobile communication devices of the personnel. The respective persons may be able to accept, delegate or reject assigned tasks by sending an appropriate response to the system, which verifies the change and might transmit a new schedule, insist on the task, or provide an alternative proposal.

Moreover, there may be display devices in the hospital for displaying the status of every patient, clinical pathway, OR and/or of related tasks. In that way the personal is able to access all relevant information. Such display devices may be, e. g., workstations or wall mounted displays in the hospital. Preferably the wall mounted displays allow interaction with the plan, in order to display more detailed information if requested. The request can be entered, e. g., via a touch screen display or by connected keyboard or mouse.

According to a preferred embodiment, the modular system includes a localisation system for locating and/or tracking the operating-room related resources. Preferably, the localisation system forms part of an OR steering and localisation module. The OR steering and localisation module locates required staff and equipment resources and manages resource usage to allow flexible planning, and real-time, task-driven control of operating room processes. In particular, the OR steering and localisation module permits locating and/or tracking of any staff, patients, mobile devices, beds, and/or further items relevant to hospital processes. Preferably this is done with a combination of different location technologies, e. g., WLAN tracking, such as infrared light location, active RFID gates or others. The OR steering and localisation module may include a flexible interface to other location technology available in the respective hospital. This interface may provide an easily configurable setting to connect the available technologies to the system without extensive configuration. This can be achieved through an interface which converts the location data from the location technology into a format compatible to the present system.

Preferably, the system also enables staff communication and/or nurse call, most preferably via internet protocol (VOIP). This may also permit the transmission and display of patient data.

In a preferred embodiment, the OR Steering & Localization Module further includes a resource steering system for controlling and adapting the workflows into and out of an operating room unit, and for alerting in case of deviation from planned pathways, reminding tasks along pathways, and/or visualisation of all operating-room related pathways in the hospital. The steering is done based on the location information and on the tasks. Every task includes required resources and a certain time-frame in which it should be completed. The tasks are distributed among the personnel that is available at the relevant time. If, for example, a certain patient needs treatment in a certain time-frame and two nurses are needed for that treatment, both receive a task for that treatment in their task lists. If the treatment is not completed in the required time-frame, alerts will be triggered. If upon the alerts there is no reaction indicating completion of the task, the alerts may be escalated to a higher level in the hierarchy of the hospital.

Preferably this alerting system also includes necessary devices for treatments. Thus, e. g., if a device is scheduled for a particular OR and does not arrive in the scheduled place at the scheduled time, the system might trigger an alarm, e.g. a sound emitted by the device itself or by an WLAN tag fixed to the device, or a call on a communication system carried along with the person transporting the device or a person near to it as detected by the localisation system.

This approach permits real-time task-driven control, optimal resource management, and identification and elimination of bottlenecks, such as lack of OR availability or unavailable staff.

Further preferred features and benefits of the OR steering and localisation module are: Visualization of OR and hospital activities, tracking of clinical pathways, measurement of deviations from plan, transparency of processes and execution of planned activities, and increased process efficiency. Reports generated by the OR steering and localisation module, in connection with the OR Resource Planning Module, may include, e. g., target-performance comparison, input of resources, duration of surgeries, changeover time, and the absence rate per resource, e. g., the time a person, a room, an instrument, or some other device or facility is not available.

According to a further preferred embodiment, the modular system comprises an OR instrument management module suitable, in particular, for automatically controlling orders, storage, delivery and/or maintenance of instruments and/or devices. The OR instrument management module optimizes instrument use by automatically tracing instrument use, manages inventories by tracking storage details, as well as delivery, usage, processing and sterilization, and maintenance of instruments.

The OR instrument management module helps optimize supply logistics. By offering accurate, standardized tracking of instruments, the OR instrument management module allows thorough documentation of instrument use and provides a sound basis for properly allocating costs to individual cases. Necessary repairs and replacements can be triggered using the OR instrument management module in the OR, reducing the time required for repair and procurement as much as possible. Thus, e. g., the pathway towards an internal or external service department might be indicated or automatically chosen for an instrument if a malfunction has been indicated, a preset number of usages or sterilizations has been counted, or a preset time has been reached.

In a preferred embodiment, a complete inventory of instruments and precise cost assessments, including assignment of instrumentation used for each step of a surgical procedure, allow effective budgeting and forecasting. Beyond that, the Instrument Management Module permits development of innovative financing concepts, such as pay-per-use and optimized repair management strategies by linking instrument usage data with respective service providers.

Further preferred features and benefits of the OR instrument management module are efficiency and transparency of instrument use, automatic control of the number and the life cycle duration of instruments, and RFID tracking of trays, the corresponding instruments being identified by a packing list. Moreover, the OR instrument management module may be preferably adapted to automatically control or place orders, storage, delivery and/or maintenance of instruments and, as well, of any kind of medical devices related to the OR. Reports generated by the OR instrument management module may include, e. g., reports on the lifecycles of instruments, the storage of instruments, and the repair cycles of instruments.

In a preferred embodiment, the OR instrument management module is designed for alerting according to the number of uses of each individual surgical instrument and/or according to sterilisation time limits. It may also be connectable to a sterilizer unit so as to automatically control the processes relating to sterilization of instruments.

Preferably, the modular system comprises an OR document management module that provides for automatic documentation of pre-, intra- and/or post-operative activities. In particular, the OR document management module provides centralized management and distribution control system for physician letters and reports. A query function simplifies report development. It can automatically place endoscopic images recorded and archived by an existing image storing system. It also allows drag-and-drop placement of images in reports with other systems. It may preferably also contain templates and predefined and/or, according to available information, pre-composed text modules for documents to be accessed by practitioners and further processed, in particular to be completed, signed, sent and stored. In particular, it may automatically generate a discharge letter based on the intra-operational documentation. Thus, operating room report writing is simplified and efficient flow of information is promoted. Furthermore, cost or income per case may be indicated.

Further preferred features and benefits of the OR document management module are an efficient online method for distributing physicians' documents as needed, transfer of procedure documentation directly to a hospital information system, preferably via a standard HL7 interface, accountability of operations, and reduced cost and effort for documentation. Finally, reliability and quality of documentation and the availability of information are increased.

Preferably, the modular system also comprises an OR anaesthesia management module for developing automated documentation of pre-, intra- and/or post-operative anaesthesia data, including live data and/or drug consumption. Thus, tracking and documenting vital parameters and anaesthetic usage for each intervention from within the sterile field are facilitated. Data can be collected automatically by the OR anaesthesia management module and maintained to use for review or to clarify any questions that may arise regarding any procedure. Reports generated by the OR anaesthesia management module may comprise, e. g., the registration of vital data, the use of medication per surgery, and daily and weekly data for each anaesthetist, for each operating room, etc.

Furthermore, the system preferably includes an automatic image storing module for automatic storage of OR-related data, such as image, patient and other data for at least a minimum time. After this time the data may be automatically deleted. Thus, all documentation requirements may be fulfilled with respect to a patient's post-operative records without wasting excessive data storage.

In a further preferred embodiment, the system also includes or communicates with an integrated OR system for controlling medical and other devices in an operating room during surgery. In this way, all tasks inside the operating room may be controlled through the integrated OR system, while being embedded in the system described according to the present invention.

Extended use of operating room integration systems has increased productivity and efficiency during many surgical procedures. The present invention takes integration in a hospital to a new level, including connectivity with hospital information systems and permitting target-oriented integration of pathways to an OR-unit, optimizing workflows and enhancing efficiency. The term "hospital" includes any hospital or office or other facility which comprises an operating room or where operating-room related tasks are performed.

Further benefits of the present invention include: Enabling hospitals to optimize operating room scheduling and time and usage of staff members, assistance in surgical pre-planning, coordination and control of the use of operating room resources, ensuring more efficient information flow between operating rooms and hospital information systems, and support in developing strategies for optimal usage, offering the ideal solution to ensure economical use of surgical suites and limited resources. By optimizing the schedule of operating room usage, hospitals can gain higher throughput in surgical departments.

By the use of standardized interfaces, a system according to the present invention can be embedded easily and simply into existing hospital IT structures. Its modular system design permits adaptation to individual hospital requirements and offers a dynamic platform to accommodate future developments and enhancements. By remote connectivity remote diagnostics and service may be facilitated as well as convenient software upgrades.

Further advantages objects of the present invention are to create transparency in the OR, which is a critical prerequisite for efficiency and revenue-increasing measures designed to secure and financially stabilize a profitable hospital. Reporting, steering and controlling options can be available to hospital administrators.

Moreover, further aspects of the present invention are master data management, image and movie storage, in particular HD image storage, and interaction with external players such as sterilizers, laboratories, physicians, etc.

DETAILED DESCRIPTION OF THE INVENTION

Figure 1:
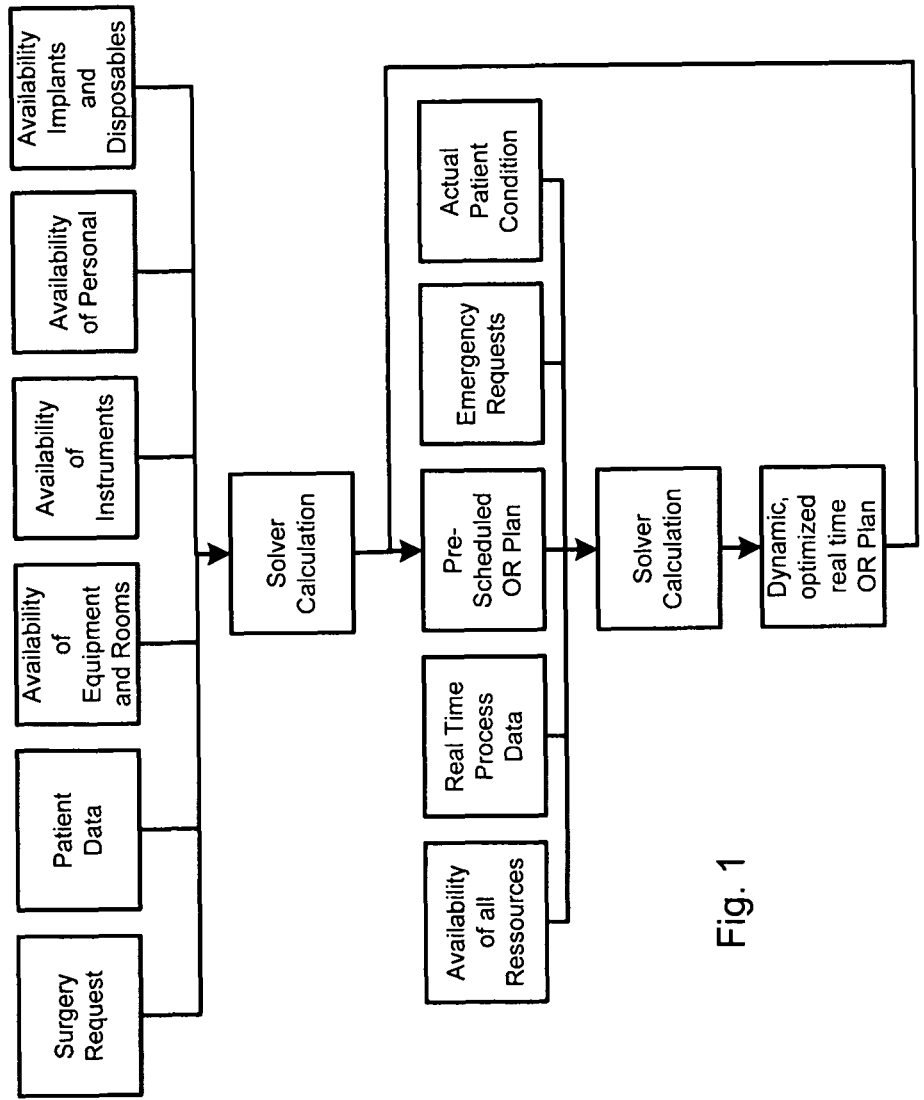
FIG. 1 is a schematic diagram of the method for managing OR resources according to a preferred embodiment of the invention.

As shown in FIG. 1, various kinds of information are processed in a method for the management of OR resources. The information is gathered from neighboring systems via interfaces.

The planning process starts with the admission of a patient in a hospital and with a surgery request concerning that patient. Through interfaces the computer on which the planning method is implemented captures all necessary data from the hospital information system or directly from neighboring systems, for example patient data. When processing the surgery request, the availability of all necessary resources is checked, based on the diagnosis of the patient. Based on those data, all dates and times are proposed when the factors needed are available in an optimized combination. All surgery requests result in a pre-scheduled OR plan, which can be established on a long term basis, well before the planned surgeries.

During the day of the surgery the plan is then put to operation. Tasks for every patient are distributed among personnel on duty, and the completion of these tasks is monitored through real time process data. After the completion of every task or due to other events, such as emergencies or changing patient conditions, the plan is recalculated and optimized. The criteria for that optimization can be set according to a hospital-specific strategy, for example maximal utilization of the operating rooms. The key to that optimization is the real time process data that is integrated in the recalculation of the current plan. It includes the location of every person who is planned in the schedule, as well as the locations and conditions of the patients. Moreover, location and usage of the devices and instruments needed in these operations can be monitored and planned.

When an emergency request occurs, the re-calculation of the schedule is based on emergency indicators; the higher the indicator is, the faster a free operation room is allocated to the patient. Through that continuous re-calculation of the plan, the hospital is always working with an optimal real-time OR plan.

Figure 2:
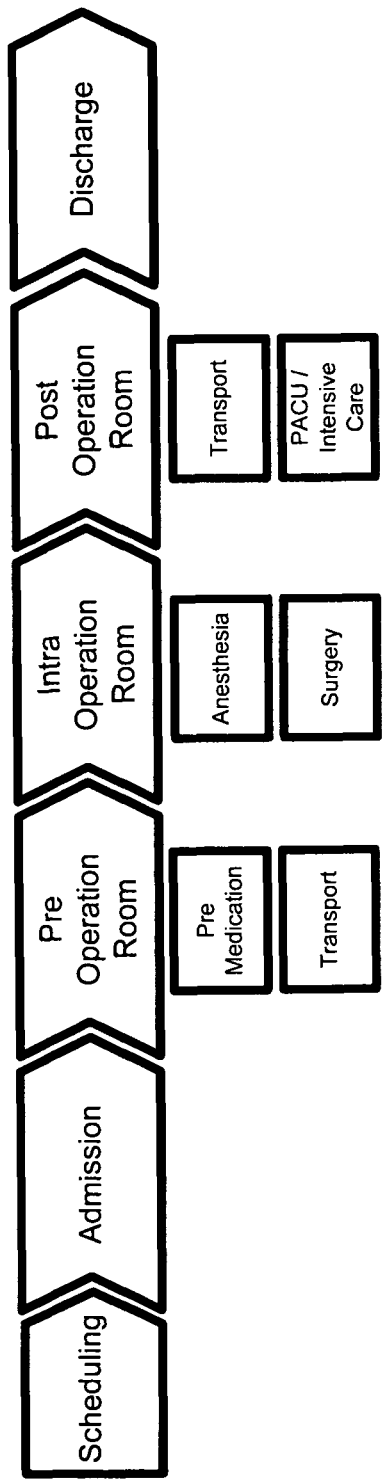
FIG. 2 shows an example for a simple clinical pathway.

FIG. 2 shows an overview of a clinical pathway. Clinical pathways show the treatment or process steps to be taken by patients in the hospital. Normally they are specific for each diagnosis; moreover, pathways offer alternatives based on patient condition and anamnesis. In FIG. 2, a general clinical pathway is shown. It includes the scheduling of the patient and the admission, when the patient comes to the hospital. Before the operation begins, the patient receives pre-medication and will be transported to the OR. In the operation room, anesthesia is introduced, and the patient is operated. After the operation, the patient is transported to the post anesthesia care unit or intensive care unit and finally back to the ward. When the patient is cured he/she is discharged from the hospital. In the method according to the invention, the clinical pathway preferably is broken down into tasks. These tasks include assigned resources and a certain time frame in which they shall be fulfilled.

Figure 3:
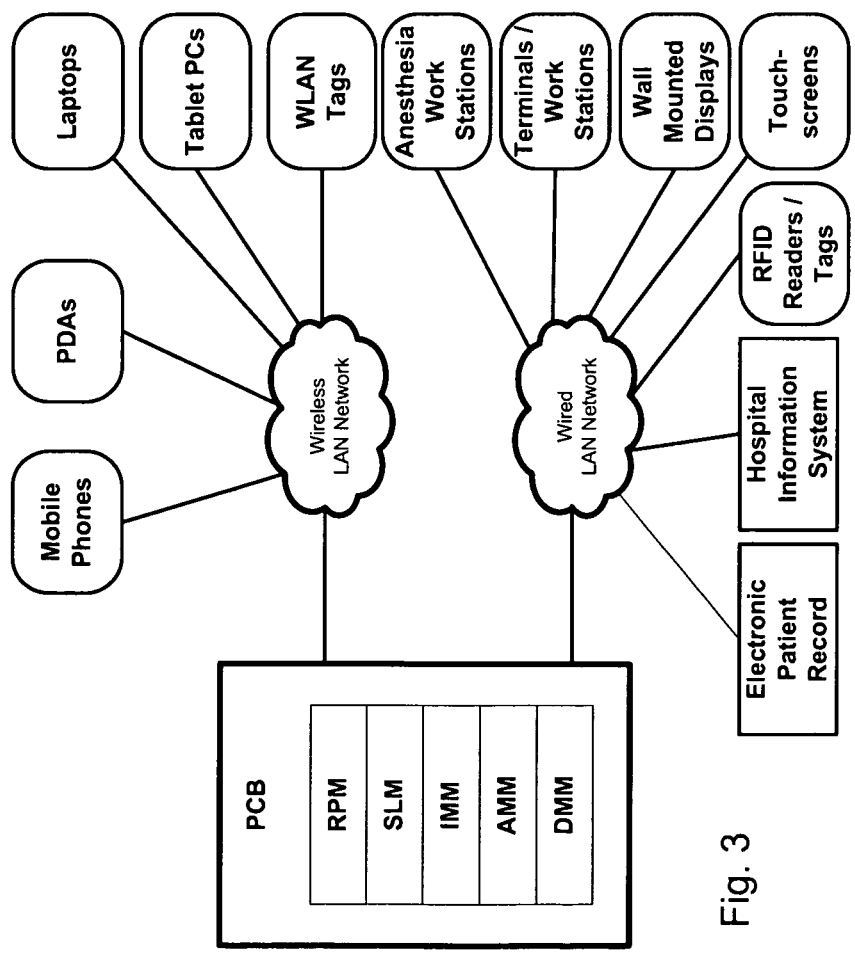
FIG. 3 gives, in schematic form, an overview of the hardware and network connections of a system according to an embodiment of the invention.

FIG. 3 gives an overview over the connected systems and hardware. The interfaces to other applications and hardware via the wired and wireless networks are provided through the process control bus of the system. It provides a freely definable interface system which allows integration of multiple systems and hardware.

The system allows access to the data via wireless and wired networks, providing user interfaces on various devices, such as mobile phones, PDAs, laptops, tablet PCs and wall mounted displays, terminals and work stations. Wireless LAN tags and the other mobile devices additionally provide location information on the devices themselves, but also on the assigned users or diagnostic and therapeutic devices carrying those tags. RFID readers and tags are necessary for locating and controlling instruments and instrument trays. They allow tracking the usage and status of the inventory.

Through the connection with the anesthesia work station the condition of the patient can be monitored and integrated into the planning and documentation. Finally, the connection to patient records and to the hospital information system allows two-way synchronization of patient data.

Figure 4:
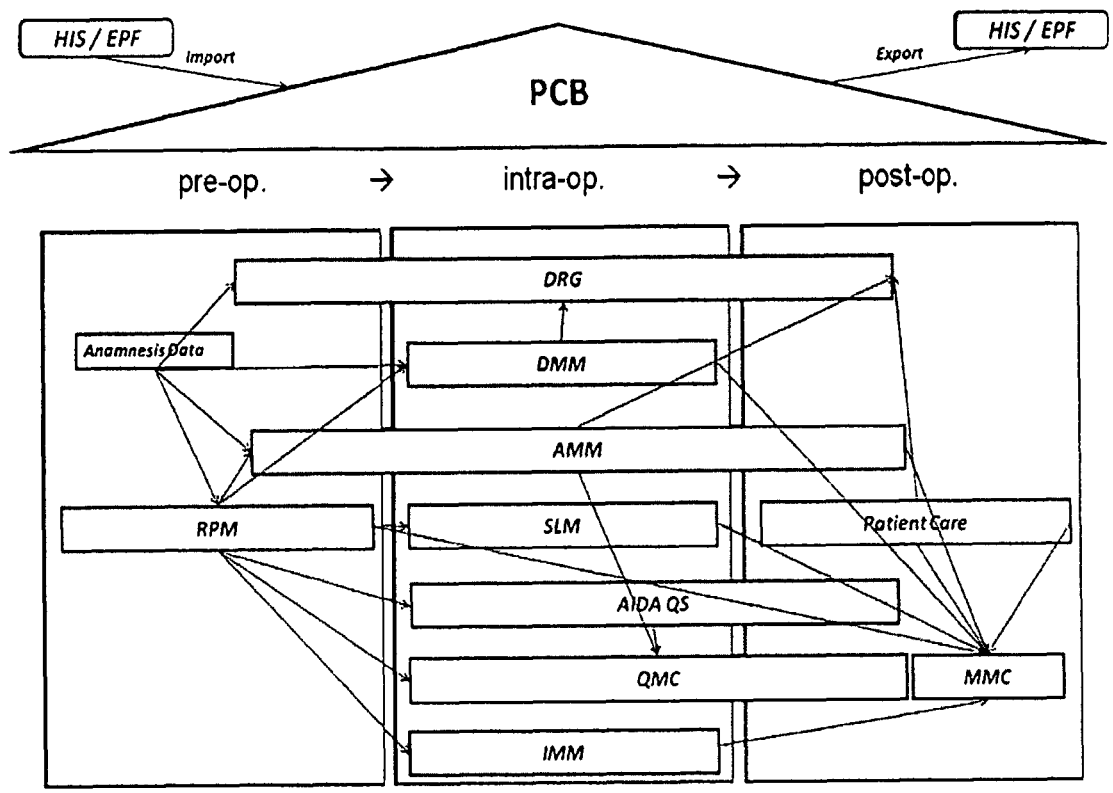
FIG. 4 shows the overall data flow in an embodiment of the invention.

As shown in FIG. 4, the present invention pertains to pre-operative as well as to intra-operative and post-operative processes in a hospital. The process control bus (PCB) that controls the modules and their interaction is symbolically depicted as the "roof" under which the individual modules work. Moreover, it provides for connections to a hospital information system (HIS) and for accessing data from and providing data to the electronic patient file (EPF). The process control bus may be based on a control unit connected via a network to other computers on which the individual modules operate, each of which may be operatively connected to further devices such as an integrated OR control system or particular devices such as RFID equipment etc. Alternatively, the process control bus and one or several modules may be implemented on a single computer. Some functions, such as nurse call via internet protocol may be independent from the process control bus.

Starting with the pre-operative phase, the patient's anamnesis data are made available to those modules relying on these data. These are, at least, the DRG (diagnosis related groups) module for processing information relevant to accounting, the document management module (DMM), the anaesthesia management module (AMM), and the resource planner module (RPM).

Based on those data, the resource planner module (RPM) provides requirement lists to all other operative modules involved in the intra-operative phase, in particular to the document management module (DMM), the anaesthesia management module (AMM), the steering and localisation module (SLM), an image data archiving system (AIDA QS), a quality control and management module (Quality Management Cockpit, QMC), and to the instrument management module (IMM). During the intra-operative phase, data are supplied by the document management module (DMM) to the DRG module, and by the anaesthesia management module (AMM) and the image data archiving system (AIDA QS) to the quality control and management module (QMC).

Finally, the modules having performed their respective tasks as described above, information is provided to the Management Cockpit (MMC) and to the DRG module in the post-operative phase. The Management Cockpit provides for configurable key performance indicators, in particular economic reporting, user individual reports, drill-down reporting, target-actual comparison, trend analysis reports, and export of data for external processing.

The preferred embodiment described features an integrated OR system, e. g. the OR1™ connect series by KARL STORZ, suitable for integration into the system described. The integrated OR system may, e. g., be suitable for accessing and processing HD images, and may provide access to X-ray, ultrasound and other PACS images during surgical procedures, monitoring of vital patient parameters, integration of images from a navigation system, and may include a CD player or OR light controls. The system may also include a unit for tele medicine, such as the KARL STORZ OR1™ TENDOS™ System. The system may further include facilities for training and external service access.

What is claimed is:

1. A computer-implemented method for managing operating-room resources in a hospital, including the steps of
   receiving at least one surgery request on a computer,
   identifying the resources required for surgery associated with the at least one surgery request,
   capturing initial data on availability of the resources required for surgery associated with each of the at least one surgery requests on said computer,
   capturing initial patient data for each of the at least one surgery requests on said computer,
   establishing a pre-scheduled operating-room plan based on an initial optimization performed on said computer,
   capturing current data on availability and location of one or more of the resources required for surgery associated with each of the at least one surgery requests on said computer,
   capturing current patient data for each of the at least one surgery requests on said computer,
   automatically detecting actual current location of one or more of said resources in real-time with a location monitoring system;
   capturing real-time data on deviations of at least one operating room related process from a pre-determined process path on said computer, where in the deviations include deviations automatically detected by means of said location monitoring system; and
   establishing a current operating-room plan based on a real time optimization performed on said computer.

2. The method according to claim 1, further comprising the step of receiving emergency requests.

3. The method according to claim 1, wherein the current data on availability of the resources and/or the current patient data are captured in real-time, and a real-time operating-room plan is established based on a real-time optimization.

4. The method according to claim 3, further comprising the step of capturing real-time data on at least one operating-room related process.

5. The method according to claim 1, further comprising the step of, if a deviation is detected, transmitting a notification to a communication device related to the deviation.

6. A Computer-based system for managing operating-room resources in a hospital, comprising at least one computer and software executing on said computer for
   receiving at least one surgery request,
   identifying the resources required for surgery associated with the at least one surgery request,
   capturing initial data on availability of the resources required for surgery associated with each of the at least one surgery requests,
   capturing initial patient data for each of the at least one surgery requests,
   establishing a pre-scheduled operating-room plan based on an initial optimization,
   capturing current data on availability of one or more of the resources required for surgery associated with each of the at least one surgery requests,
   capturing current patient data for each of the at least one surgery requests,
   automatically detecting actual current location of one or more of the resources in real-time with a location monitoring system;
   capturing real-time data on deviations of at least one operating room related process from a pre-determined process path, where in the deviations include deviations automatically detected by means of said location monitoring system; and
   establishing a current operating-room plan based on a current optimization.

7. A modular system for managing operating-room related processes in a hospital, including
   a control unit for operating a process control bus for controlling at least one operating-room related process in the hospital,
   said control unit including a solver engine for optimizing said at least one operating-room related process;
   a localisation system controlled by said process control bus, adapted to locate and/or track the current actual availability and/or current actual location of one or more operating room resources in real time;
   the control unit being connectable in a modular manner to a multiplicity of modules, and
   at least one of a multiplicity of modules operatively connected to the control unit, the module controlling at least one task in an operating-room related process in the hospital.

8. The modular system according to claim 7, further comprising an operating-room resource planner module for planning operating-room resources.

9. The modular system according to claim 7, further comprising an operating-room resource steering system for steering the workflows into and out of an operating room unit, alerting in case of deviation from planned pathways, reminding tasks along pathways, and/or visualisation of all operating-room related pathways in the hospital.

10. The modular system according to claim 7, further comprising an instrument management module for alerting according to the number of uses of surgical instruments and/ or to time limits for the use of surgical instruments or material, in particular sterilisation limits.

11. The modular system according to claim 10, wherein said instrument management module is operatively connectable to a sterilizer unit.

12. The modular system according to claim 7, further comprising an automatic documentation system for automatic documentation of pre-, intra- and/or post-operative activities.

* * * * *